United States Patent [19]

Murphy et al.

[11] Patent Number: 5,046,624
[45] Date of Patent: Sep. 10, 1991

[54] SURGICAL INSTRUMENT STAND

[76] Inventors: Susan A. Murphy; Paul G. Murphy, both of 3929 Highway U, Warrenton, Mo. 63383

[21] Appl. No.: 566,141

[22] Filed: Aug. 13, 1990

[51] Int. Cl.$^5$ .............................................. A47F 7/00
[52] U.S. Cl. ................................. 211/70.6; 206/370; 248/176
[58] Field of Search ................ 211/70.6, 70.7; 248/176, 316.8, 309.2; 206/369, 370

[56] References Cited

U.S. PATENT DOCUMENTS

| | | | |
|---|---|---|---|
| 3,696,920 | 10/1972 | Lahay | 206/370 |
| 3,925,014 | 12/1975 | Langdon | 206/370 X |
| 4,229,420 | 10/1980 | Smith et al. | 206/370 X |
| 4,305,629 | 12/1981 | Friis | 211/70.6 X |
| 4,342,391 | 8/1982 | Schainholz | 211/70.6 X |
| 4,512,466 | 4/1985 | Delang | 211/70.6 X |
| 4,577,755 | 3/1986 | Ramsay | 206/370 |
| 4,641,749 | 2/1987 | Link et al. | 211/70.6 X |
| 4,643,303 | 2/1987 | Arp et al. | 206/370 |
| 4,865,821 | 9/1989 | Langdon | 206/370 X |

Primary Examiner—David L. Talbott
Attorney, Agent, or Firm—Hovey, Williams, Timmons & Collins

[57] ABSTRACT

A surgical instrument stand useful for the compact organizing and counting of a plurality of ring-handled surgical instruments being held in a parallel and vertical position. The stand is formed of autoclavable polymeric material and embodies an elongated rectangular body with the lower portion or base having a top wall acting as a resting wall for the surgical instruments. Vertical compartments are formed from equal distant partitions thus holding the ring-handled surgical instruments in a vertical position for easy use and stability during surgery. An adhesive strip on the bottom stabilizes the stand in relation to other surfaces.

10 Claims, 1 Drawing Sheet

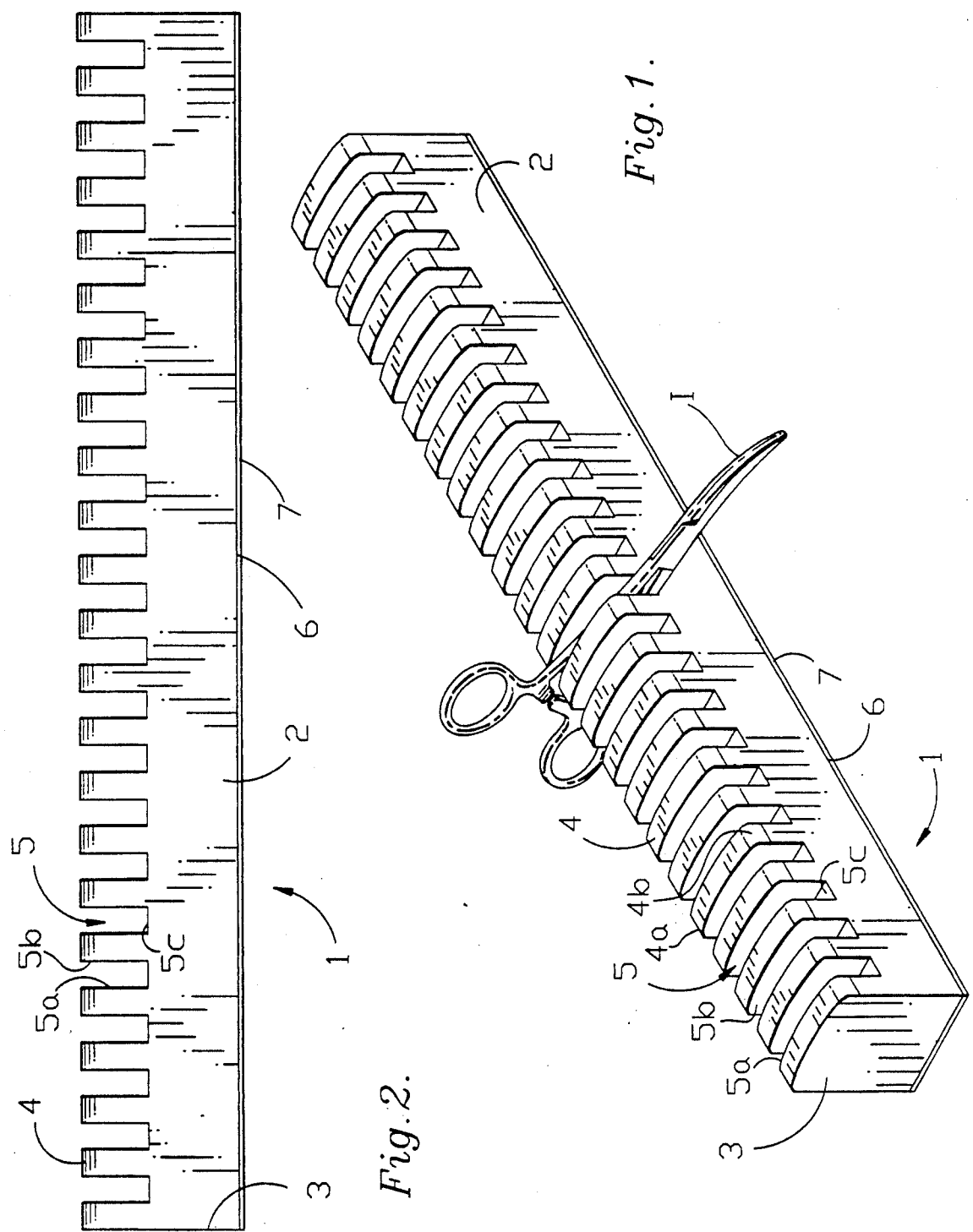

SURGICAL INSTRUMENT STAND

BACKGROUND OF THE INVENTION

1. Field of the Invention

This invention relates in general to surgical stands and in particular to a surgical stand for ring-handled surgical instruments.

2. Description of the Prior Art

Much effort is taken in surgical procedures to sterilize and count surgical instruments. However less effort is utilized in holding sterilized ring-handled instruments in a vertical position during surgery since current medical practice attempts to balance the ring-handled instruments vertically with the ring-handles extending just over a rolled towel which sits on a small surgical stainless steel instrument table. This practice presents problems since the towel obviously can not hold the instruments securely since it won't mold perfectly or generally to the shape of the instruments. A number of these instruments need to sit along side and touch each other on the towel to maintain the vertical position of the instruments.

The instruments can easily fall over by bumping, doctors throwing instruments which hit these vertical instruments and the small surgical instrument table being bumped or pushed. Not only does this mix-up the instruments, but it also greatly slows and hampers the assisting personnel in the performance of their duties.

A few instrument stands, racks and trays are recognized in the prior art, but none provide a compact, inexpensive and easily used solution to this problem. Prior art patents and catalogs for these stands, racks and trays are briefly described below.

The Meinecke et. al. U.S. Pat. No. 1,538,571 shows a rectangular thermometer holder where the thermometers can rest in specially shaped recesses which protrude upward close to the two ends. This holder is obviously designed for thermometers and can not be adapted to hold ring-handled surgical instruments.

The Bates U.S. Pat. No. 2,018,651 shows a square sterilizing and operating instrument tray which has specially molded clips at one end to hold straight-handled instruments at an angle. The holder in the Bates Patent could not be easily adapted to accept other forms of surgical instruments--especially ring-handled instruments. Even if ring-handled instruments could fit in the loops, they would fall over too easily due to lack of support.

The Son U.S. Pat. No. 2,472,028 discloses a rectangular sterilizing tray for hypodermic needles which is obviously designed for sterilization of hypodermic needles on specially molded forms that can be moved due to being hinged. This tray can not be adapted for other instruments.

The Golightly U.S. Pat. No. 3,484,226 illustrates a rectangular mold for supporting glass sheets in a vertical position using guiding rails. This has little value for supporting surgical instruments.

The Smith et. al. Pat. No. 4,229,420 discloses a surgical instrument rack which comprises two sections that must be separated to load or unload the rack. A wall and partitions are set to one side of the support member upon which ring-handled instruments can be set. It is readily apparent that this rack holds ring-handled surgical instruments but the aperture and retaining member which partially opens the instrument jaws obviously make Smith's Patent better used for sterilization and transport than for use during surgical procedures. When attempting to use it for an instrument stand for surgical procedures, it becomes awkward and difficult to use. The retaining member must be removed before the instruments can be used. Upon opening this could result in the instruments falling out and being contaminated if the tabs get hung up and make opening difficult. If this is constructed from polymeric material the partitions could more readily fracture or break. It has been suggested that the partitions could be cut by hand and removed to allow several similar instruments to touch, support each other and be grouped in the rack. This presents several difficulties: The loops can not be replaced after detached, the instruments can not stand separated for good sterilization, the rack can not be used for other groups of similar instruments with different quantities in each group. Instruments could fall over if groups did not fill the cut-out partition area. If it is disposed of after each use there would be a lot of detachment needed for each new rack used. This rack is not as compact. If constructed from stainless steel the rack would be very expensive—an obvious drawback.

The Surgical Armamentarium catalog, V. Mueller Operating Room Division of Baxter Healthcare Corporation, p. F123 (1988), reveals a spring looking instrument holder and a similar type spring holder mounted on a flat rectangular instrument tray. The difficulties with these type of spring holders are the high prices required to purchase the metal holders, as well as the great possibility that the surgical instruments can readily be inserted into the holder in such a wrong and misaligned fashion so as to get their tips into a wrong compartment of the spring and thus get tangled and stuck in the spring holder. This problem is caused by lack of a complete separation wall between the compartments.

Whatever the precise merits, features and advantages of the above cited references, none of them achieves or fulfills all the purposes of greater simplicity, compactness, economy, stability, easiness of use, convenience, organization, and support of instruments which this present invention accomplishes.

SUMMARY OF THE INVENTION

The principle object of the present invention is to provide a stand to maintain ring-handled surgical instruments in a vertical parallel position to better facilitate the organization of said instruments during surgery.

It is also an object of the present invention to provide such a device which is of inexpensive construction.

Another object is to provide such a device that is compact and thus easily used on a small instrument table.

A further object is to provide such a device which will reduce wasted time before, during and after surgery. This is effectively accomplished since ring-handled instruments can more quickly be set up in their vertical position without fear of falling over. This stand eliminates the need to manually roll the towel that holds the instruments as is customary current practice. This is especially critical during emergency surgeries when time is of the essence. During surgery time is better saved by the present invention since the instruments can not be readily knocked over knocked on the floor or mixed-up. Time is saved also at different times during surgery since the instruments are more easily counted in their vertical position.

A further object is to provide such a device which is stable and thus will not move.

The present invention includes a one-piece, elongated, integrally formed body which is provided with a base having a top wall that acts as a resting wall. A plurality of spaced partitions project upwardly from the base, thus creating a series of solid-sided and solid-floored compartments which can receive ring-handled instruments which will be able to remain in a vertical plane. The ring handles extend on one side of the compartment with the remaining portion of the instrument in or extending out the other side of said compartment. A covered adhesive strip covers the entire bottom of the device so that when the adhesive is uncovered, the stand can easily adhere to numerous types of surfaces and thus have even greater stability.

BRIEF DESCRIPTION OF THE DRAWINGS

FIG. 1 is a perspective view of the surgical instrument stand in accordance with the present invention, illustrating how it vertically supports a ring-handled surgical instrument.

FIG. 2, is a front elevational view of the stand.

DETAILED DESCRIPTION

Refer now to FIG. 1, which is an overall drawing of a preferred embodiment of the invention.

The numeral 1 generally designates the surgical instrument stand for supporting ring-handled surgical instruments in a vertical and parallel position. This one-member unit is an elongated and generally rectangular body laying generally horizontal and is preferably molded from strong, relatively rigid polymeric material capable of withstanding autoclaving temperatures and processes. This enables the stand to be more economical and lighter weight. Having only one member in the unit makes this stand simpler to use.

The lower portion or base 2 of the stand rises to about one half the total height of the stand and has a flat top wall that acts as an elongated generally rectangular resting wall for the upper partition walls as well as ring-handled instruments. This base 2 can be hollow.

The ends 3 of the stand are molded integrally from the same material as the base and partitions.

The upstanding, transverse partitions 4 are molded as one integral part with the base 2 in an aligned row and protrude upward in a vertical plane at equal spaced intervals thus creating a series of open-top compartments 5 above the base 2 for receiving ring-handled surgical instruments. Each compartment has a front-to-rear orientation. Each partition 4 has a pair of oppositely facing planar surfaces that rise from the top wall of the base 2 and span the distance between the front and rear sides of the body whereby to define solid sidewalls 5a and 5b for the compartments 5. The top wall of the base 2 serves as a solid floor 5c for the compartments. The sidewalls 5a and 5b are parallel to one another and intersect the floor 5c at right angles. The tops of the partitions 4 are slightly rounded and intersect with the front and rear sides of the body at locations 4a and 4b spaced above the floor 5c. The instruments I are easily inserted into the compartments 5 and lay in those compartments on edge resting on the floor 5c and confined by sidewalls 5a and 5b. As shown in FIG. 1, the base of the stand is much narrower than the length of the instrument. The instruments' ring handles thus extend out the back side of the compartments 5 as a remaining portion of the instruments extend out the front side of the compartments 5 and rest on a table. This configuration makes it easier to mount ring-handled instruments in a vertical parallel position since it can be done more quickly and avoids the lengthier process of rolling a towel on which to mount instruments.

Counting instruments before, during and after surgery is better facilitated by this stand which keeps the instruments organized. This is especially helpful in emergency cases when time is of the essence.

Mounting instruments on this stand provides greater stability for the instruments which can not be easily knocked over and mixed-up due to bumping, throwing of other instruments and any other possible interference.

This stand has a bottom 6 under the base 2 which provides a stable and relatively smooth surface to allow the application of a covered adhesive strip 7 adhered to the bottom 6. The adhesive strip 7 should cover virtually all the bottom 6. The adhesive strip 7 cover can be removed from the adhesive strip, thus allowing the adhesive strip and instrument stand to adhere to many surfaces, thus providing greater stability to the stand by preventing it from being pushed, knocked over or moved in any manner. This keeps the instruments better organized.

FIG. 2 clearly shows the general spacing relationship of the partitions 4 and compartments 5.

This surgical instrument stand can be made in varying sizes but the generally preferred size of 11¼ inches wide, 1½ inches high and 1 3/16 inches deep maintains its compact characteristics for easier use and handling.

What has been described has fulfilled the objects of the invention since it has been shown how the stand enables parallel and vertical positioning of ring-handled surgical instruments thus allowing better organization of the instruments. It is economical and compact and will reduce wasted time before and after surgery due to its stability and elimination of manual towel rolling. This is critical during emergencies.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A stand for use in supporting a plurality of ring-handled surgical instruments in an ordered series with each instrument held upright and on edge in generally parallel relationship with the other instruments in the series, said stand comprising:
    an elongated, one-piece, unitary body having a longitudinally extending base and a plurality of upstanding transverse partitions integral with and projecting upwardly from said base,
    said partitions being arranged in an aligned row extending longitudinally from one end to the other end of the base and in longitudinally spaced relations to one another to present a longitudinally extending series of transverse, open-top, instrument-receiving compartments immediately above and along the length of the base,
    said base having a top wall spanning the distance between front and rear sides of the body whereby to define a solid floor for each of said compartments respectively, and each of said partitions having oppositely facing planar surfaces rising from said floor and spanning the distance between the front and rear sides of the body whereby to define a pair of solid and planar sidewalls for each of said compartments respectively, said base having a width which is substantially less than the length of the instruments to be supported by the stand whereby when the stand is placed on a supporting surface with the base resting on the surface and the compartments facing upwardly, instruments inserted into the compartments project outwardly in opposite directions beyond the front and rear sides of the body and into superimposed relationship with the supporting surface.

2. A stand as claimed in claim 1, said sidewalls for each compartment being disposed in parallel relationship with one another and intersecting the floor at right angles.

3. A stand as claimed in claim 2, each of said partitions having a rounded top extending transversely between the front and rear side of the body and intersecting with said front and rear sides at locations spaced above said floor.

4. A stand as claimed in claim 3, said partitions being equally spaced along the length of the base to present compartments of equal width.

5. In a stand as claim in claim 4, said body being molded from a relatively rigid polymeric material capable of withstanding autoclaving temperatures.

6. In a stand as claimed in claim 5, said base having a bottom surface provided with an adhesive layer for use in retaining the stand in place on a supporting surface.

7. In a stand as claimed in claim 1, each of said partitions having a rounded top extending transversely between the front and rear sides of the body and intersecting with said front and rear sides at locations spaced above said floor.

8. In a stand as claimed in claim 1, said partitions being equally spaced along the length of the base to present compartments of equal width.

9. In a stand as claimed in claim 1, said body being molded from a relatively rigid polymeric material capable of withstanding autoclaving temperatures.

10. In a stand as claim in claim 1, said base having a bottom surface provided with an adhesive layer for use in retaining the stand in place on a supporting surface.

* * * * *